US006465012B2

United States Patent
Vilkov

(10) Patent No.: US 6,465,012 B2
(45) Date of Patent: *Oct. 15, 2002

(54) PHARMACEUTICAL TABLET FORMULATION CONTAINING GABAPENTIN WITH IMPROVED PHYSICAL AND CHEMICAL CHARACTERISTICS AND METHOD OF MAKING THE SAME

(75) Inventor: Zalman Vilkov, Dingman's Ferry, PA (US)

(73) Assignee: Purepac Pharmaceutical Co., Elizabeth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/873,994

(22) Filed: Jun. 6, 2001

(65) Prior Publication Data

US 2001/0043946 A1 Nov. 22, 2001

Related U.S. Application Data

(63) Continuation of application No. 09/379,604, filed on Aug. 24, 1999, now Pat. No. 6,294,198.

(51) Int. Cl.[7] ............................................... A61K 9/20
(52) U.S. Cl. ...................................... 424/465; 424/464
(58) Field of Search ............................. 424/464, 465, 424/474, 475, 476, 480, 482

(56) References Cited

U.S. PATENT DOCUMENTS

| 4,024,175 | A | | 5/1977 | Satzinger et al. |
| 4,036,948 | A | * | 7/1977 | Kitamori et al. ............... 424/32 |
| 4,087,544 | A | | 5/1978 | Satzinger et al. |
| 4,533,674 | A | | 8/1985 | Schmidt et al. |
| 4,605,666 | A | | 8/1986 | Schmidt et al. |
| 4,710,519 | A | | 12/1987 | Finnan et al. |
| 4,874,614 | A | | 10/1989 | Becker |
| 4,894,476 | A | | 1/1990 | Butler |
| 4,960,931 | A | | 10/1990 | Butler |
| 5,084,479 | A | | 1/1992 | Woodruff |
| 5,534,551 | A | | 7/1996 | Page et al. |
| 5,725,884 | A | | 3/1998 | Sherwood |
| 5,792,796 | A | | 8/1998 | Woodruff et al. |
| 5,906,832 | A | * | 5/1999 | Jao et al. ..................... 424/465 |
| 6,054,482 | A | | 4/2000 | Augart et al. |
| 6,294,198 | B1 | * | 9/2001 | Vilkov ......................... 424/465 |
| 2002/0012679 | A1 | | 1/2002 | Bruna et al. |

FOREIGN PATENT DOCUMENTS

| IE | 3089/90 | 10/1995 |
| WO | 98/28255 | 7/1998 |

OTHER PUBLICATIONS

Product label for Neurontin® (Gabapentin Capsules and Gabapentin Tablets), revised Feb. 1999.
Product label for Neurontin® (Gabapentin) capsules, tablets and oral solution, FDA approved labeling text dated Oct. 12, 2000.

* cited by examiner

Primary Examiner—James M. Spear
(74) Attorney, Agent, or Firm—Burns, Doane, Swecker, Mathis, L.L.P.

(57) ABSTRACT

A pharmaceutical formulation form with improved physical and chemical characteristics, comprising gabapentin in tablet form for oral administration. The tablet form can be prepared by spray-coating gabapentin with a binder solution and compressing the spray-coated gabapentin into non-friable, stable tablets. This method is particularly useful for tablet formulations that require large doses of active drug.

10 Claims, 3 Drawing Sheets

Gabapentin Tablets, 600 mg
Effect of the Processing Method on the Tablet Hardness

PHARMACEUTICAL TABLET FORMULATION CONTAINING GABAPENTIN WITH IMPROVED PHYSICAL AND CHEMICAL CHARACTERISTICS AND METHOD OF MAKING THE SAME

This application is a continuation of application Ser. No. 09/379,604, filed on Aug. 24, 1999, U.S. Pat. No. 6,294,198.

BACKGROUND OF THE INVENTION

1. Field of the Invention

This invention is generally directed to pharmaceutical formulations with improved physical and chemical characteristics, comprising gabapentin in tablet form for oral administration. The tablet form can be prepared by spray-coating gabapentin with a binder solution and compressing the spray-coated gabapentin into non-friable, stable tablets. This invention is also generally directed to a method of producing pharmaceutical formulations in tablet form which contain large doses of active drug by spray-coating the active drug with a binder solution and compressing the spray-coated active drug into tablets.

2. Description of the Related Art

Prior art methods for improving the compression characteristics of pharmaceutical formulations involve introducing additional excipients, such as microcrystalline cellulose, as compression aids to prevent fracturing of granules and tablets. However, the inclusion of additional excipients can be expensive and time consuming, can effect the stability of the active drug agent, and can increase the size of the tablet.

Other methods for improving the compression characteristics of pharmaceutical formulations include dissolving the active drug in a binder solution to form a drug solution, spray drying the drug solution to form a powder and then compressing the powder into a tablet. This method, however, is inefficient because it requires a large amount of binder solution. Moreover, dissolving the active drug in a solution can cause stability problems, polymorph conversion, and changes in the crystalline structure of the drug.

U.S. Pat. No. 4,874,614 issued to Becker, discloses a method of preventing the fracture of coated drug granules during the compression process by incorporating into a matrix, along with the granules, microcrystalline cellulose in the amount from 10% to 50% by weight of the total matrix.

U.S. Pat. No. 5,725,884, issued to Sherwood et al., discloses the use of a microcrystalline cellulose based excipient comprising microcrystalline cellulose and silicon dioxide to improve the compressibility of the excipient microcrystalline cellulose, not the active drug substance.

U.S. Pat. No. 5,534,551, U.S. Pat. No. 4,533,674, U.S. Pat. No. 4,605,666 and U.S. Pat. No. 4,710,519 all disclose a method of producing a compressible tablet by dissolving the active agent in a solvent and a binder then spray drying the solution to obtain a spray dried powder that is suitable for direct compression.

IE 3089/90 to issued Augart, et. al., discloses a process for stabilizing pharmaceutical compositions containing gabapentin in solid form. The process entails hydrolyzing gabapentin with a semi-concentrated mineral acid and then converting gabapentin into a solid pharmaceutical composition containing hydroxypropyl methylcellulose, polyvinylpyrrolidine, crospovidone, maize starch, cyclodextrin, talcum, co-polymer of dimethylaminomethacrylic acid and/or neutral methacrylic acid ester.

Various patent applications and patents disclosing processes for preparing the gabapentin, and its methods of use are disclosed in PCT 98/28255, U.S. Pat. No. 4,024,175, U.S. Pat. No. 4,087,544, U.S. Pat. No. 5,084,479, U.S. Pat. No. 4,960,931, and U.S. Pat. No. 4,894,476.

BRIEF SUMMARY OF THE INVENTION

It has been discovered that pharmaceutical formulations containing the active drug gabapentin can be produced with large doses of gabapentin but still be small enough for a patient to swallow. It has also been discovered that pharmaceutical formulations containing gabapentin in tablet form can be produced having improved characteristics such as hardness, friability and stability. It has further been discovered that the pharmaceutical formulations containing gabapentin can be produced in tablet form by spray-coating gabapentin particles with a binder solution and compressing the spray-coated particles into tablets. This method is also applicable to other pharmaceutical tablet formulations that require large doses of active drug for oral administration.

Thus, one aspect of the present invention is a pharmaceutical tablet comprising more than about 76% by weight of gabapentin. A second aspect of the invention is a pharmaceutical tablet comprising more than about 76% by weight of gabapentin, a friability of less than about 1%, a hardness of about 10 kp to about 20 kp and a lactam level, a major degradation product of gabapentin, of less than about 0.4% by weight of the tablet composition.

A first preferred embodiment of the invention is that the pharmaceutical tablet comprises more than about 88% by weight of gabapentin. A second preferred embodiment is that the tablet has a friability of less than about 0.8%. A third preferred embodiment is that the tablet has a hardness of about 14 kp to about 16 kp. A fourth preferred embodiment of the invention is that the tablet has a lactam level of less than 0.2%.

An additional aspect of the invention is a pharmaceutical tablet comprising more than about 76% by weight of gabapentin, said tablet being formed from gabapentin particles spray-coated with a binder solution, mixed with a disintegrant and a lubricant, and then compressed into the tablet.

Another aspect of the invention is a method of producing a pharmaceutical tablet comprising:
  dissolving binder in a solvent to produce a binder solution;
  spray-coating the binder solution on gabapentin particles to achieve spray-coated gabapentin particles; and
  compressing the spray-coated gabapentin particles into a tablet for oral administration to a patient,
where the tablet contains more than 76% by weight of gabapentin.

A further aspect of this invention is a method of producing a pharmaceutical tablet comprising:
  dissolving binder in a solvent to produce a binder solution;
  spray-coating the binder solution on active drug particles to achieve spray-coated active drug particles; and
  compressing the spray-coated active drug particles into a tablet for oral administration to a patient,
where the tablet contains about 500 mg to about 1200 mg of active drug.

With the foregoing and other objects, advantages and features of the invention that will become herein after apparent, the nature of the invention may be more clearly understood by reference to the following detailed description and to the appended claims.

DETAILED DESCRIPTION OF THE INVENTION

Figure 1:
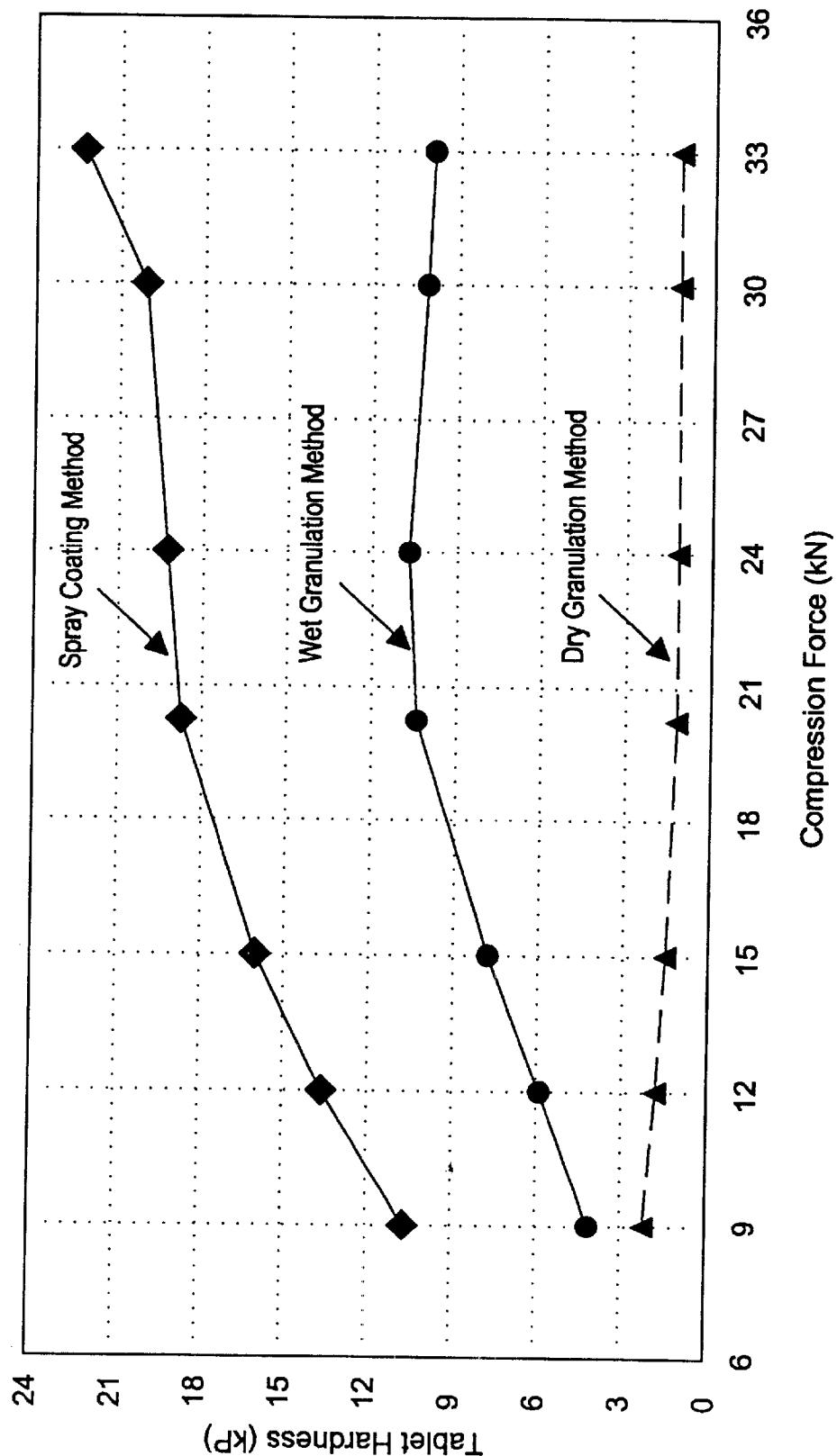
FIG. 1 shows a plot of tablet hardness versus compression force for tablets produced by traditional dry and wet granulation methods versus tablets made in accordance with Example 1.

The development of a pharmaceutical composition is often a laborious task. However, if the active drug has poor compressibility and compaction properties, developing economically efficient manufacturing processes can be painstaking. Additionally, if the active drug is incompatible with excipients commonly used in pharmaceutical formulations, the task of developing the pharmaceutical composition may require extensive experimentation. This task can be further complicated by size limitations of a tablet to be comfortably swallowed by the patient, dissolution rate limitations for bioavailability considerations and durability requirements to successfully survive the film coating process or other handling procedures. These problems were overcome in the preparation of a pharmaceutical composition for this invention.

According to the "Physician's Desk Reference®", 53$^{rd}$ Edition, Copyright 1999 Medical Economics Company, Inc., page 2302, gabapentin is used for adjunctive therapy in the treatment of partial seizures with and without secondary generalization in adults with epilepsy. Gabapentin exists in a crystalline form and exhibits poor compressibility and compactibility. Compressibility is the ability of a powder to decrease in volume under pressure, while compactibility is the ability of a powder to be compressed into a tablet of a certain hardness or crushing strength. These detrimental characteristics of gabapentin cause capping and lamination defects during compression of gabapentin into tablets. A capping defect means that there is partial or complete separation of the top or the bottom crowns of a tablet from the main body. A lamination defect means that there is a separation of a tablet in two or more layers.

The conventional approach to remedying these tableting problems is to introduce excipients as compression aids. However, the inclusion of additional excipients can adversely affect the stability of gabapentin. Also, the more excipients used in a composition the more expensive and time-consuming commercial production becomes. Furthermore, an increase in the amount of excipients results in an increase in the tablet size. Large tablets are uncomfortable to swallow and result in low patient compliance.

Excipients are substances used in combination with an active ingredient to produce a pharmaceutical formulation. Some examples of excipients are binders, lubricants, disintegrants, diluents, colorants, flavors, glidants, surfactants, absorbants and sweetening agents. Excipients often used as compression aids are binders. Binders are agents used to add cohesion to particles. Typically, materials used as binders are water-soluble derivatives of cellulose, gelatins, sugars, natural and synthetic gums, polyethylene glycol, pregelatinized starch, povidone, copolyvidone, waxes, and other suitable materials known to those skilled in the art.

The problem encountered with the inclusion of large amounts and/or number of excipients to a gabapentin formulation is that a number of excipients were not compatible with gabapentin and resulted in stability problems such as degradation. Gabapentin has been found to degrade into lactam, resulting in a decrease in the potency of gabapentin over time. Therefore, it is necessary to avoid degradation of gabapentin over the shelf life of the product. The shelf life of the product is generally two years from completion of manufacture. The level of degradation over the shelf life of the tablets can be determined by storing the product in closed containers for a three-month period at 45° C. and 75% relative humidity. Tablets containing gabapentin should have no more than about 0.4% by weight of lactam as determined by High Performance Liquid Chromatography (HPLC) at the end this three-month period. Preferably, gabapentin tablets should contain no more than about 0.2% by weight of lactam. By using methods such as HPLC or Thin Layer Chromatography for the analysis of degradation products, including lactam, one may determine the compatibility of excipients.

Another difficulty encountered in producing gabapentin tablets is that gabapentin is not amenable to traditional wet granulation techniques. Because the viscosity of the binder solution increases with an increase in the binder content, to apply a functional amount of binder for gabapentin, the amount of solvent has to be increased. This results in a wet granulation that is in a semi-liquid state and is not suitable for conventional drying methods. Therefore, the wet granulation technique has to be done in multiple stages where a portion of binder solution is added, followed by drying, then the next portion of binder solution and so forth. The wet granulation process is also conducted at elevated temperatures and accompanied by wetting gabapentin, which may be detrimental to the stability of gabapentin, cause polymorph conversion and change the crystalline structure of the active drug. This problem is eliminated by using a spray-coating method wherein a binder is dissolved in a solvent to form a binder solution which is then spray-coated on the drug particles. By using this method substantially all of the solvent is evaporated as it is applied, leaving a film of binder around the drug particles, and the process is conducted at or below room temperature.

In accordance with the present invention, spray-coating techniques are used to produce a compressible granulation containing gabapentin. Spray-coating gabapentin particles with a suitable binder solution produces a material that can be compressed into tablets having high hardness, low friability, and a size patients can swallow. Preferably, the pharmaceutical tablet comprises more than about 76% by weight of gabapentin. More preferably, the pharmaceutical tablet for commercial production comprises more than about 88% by weight of gabapentin. The tablets of the present invention can contain from about 500 mg to about 800 mg of gabapentin. More preferably the tablets will contain about 600 mg to 800 mg of gabapentin.

The spray-coating method of the present invention has application to other active drugs that exhibit poor compressibility and compactibility, are in tablet form, and require large doses for administration. Using a traditional wet granulation method to produce tablets containing large doses of active drug is inefficient and expensive because of the large amount of excipients and solvent needed to produce a suitable tablet. Furthermore, these excipients can affect the physical and chemical characteristics of the active drug rendering the product unsuitable for commercial production. By spray-coating the active drug particles with binder solution, the use of additional excipients can be avoided. Thus, tablets produced by this method exhibit acceptable physical and chemical characteristics while being small enough for a patient to swallow. A large dose of active drug is generally about 500 mg to about 1200 mg of drug content in a single tablet. The term active drug is defined as an active ingredient that is intended for use in the diagnosis, cure, mitigation, treatment or prevention of disease in humans or other animals.

In the present invention any binder solution known to form a suitable spray solution can be used. For example, binders such as water-soluble derivatives of cellulose, gelatins, sugars, natural and synthetic gums, polyethylene glycol and combinations thereof, dissolved in a solvent such as ethanol, isopropyl alcohol, methanol, methylene chloride, acetone or combinations thereof, can by used. Preferably, the binder solution comprises hydroxypropyl cellulose dissolved in an alcohol, such as ethanol.

The solution may be prepared by any method that permits dissolution of binder to produce a homogenous solution, mixture or dispersion, such that formulations may be prepared that will contain a uniform amount of the binder. The concentration of binder in solution will depend upon the components used and the desired viscosity. For example, a binder solution can have up to 30% of povidone or copolyvidone. This binder solution is sprayed onto the gabapentin particles at a controlled temperature and airflow. Gabapentin is commercially available in a variety of particle size ranges such as about 10 µm to about 250 µm. Preferably the particle size range is about 25 µm to about 75 µm. Examples of suitable commercial spray-coating techniques are described, for example, in "Spray Drying Handbook", $4^{th}$ ed., K. Masters, which is incorporated by reference.

A preferred method of spray-coating involves the use of fluid-bed processing equipment. Fluid-bed processing involves the use of air that passes up through the gabapentin particles and fluidizes them. The binder solution is applied to the particles through a pneumatically atomized nozzle equipped in the fluid-bed processing equipment. The solvent from the binder solution is concurrently removed from the coated particles under controlled temperature and airflow conditions than can be obtained by routine experimentation. By maintaining the ratio of airflow to spray rate of binder solution, an isothermic process can be achieved. This allows the application of a large amount of binder solution in a one step process while eliminating excessive heat and moisture that can be detrimental to the stability of gabapentin.

The resulting spray-coated drug particles can be subjected to direct compression tabletting methods. Preferably, other excipients such as lubricants are blended into the particles by known methods to aid compression. Lubricants are agents that prevent adhesion of the tablet material to surfaces, including dies and punches of the tablet press. Lubricants also reduce interparticle friction, facilitate ejection of the tablets from the die cavity and may improve the flow rate of the tablet material. Commonly used lubricants include, but are not limited to, talc, magnesium stearate, calcium stearate, stearic acid, waxes, hydrogenated vegetable oils and polyethylene glycol.

Optionally, disintegrants may also be added to the spray-coated drug particles. Disintegrants are agents that aid in the disintegration of the tablets and include, but are not limited to, starch, clays, microcrystalline cellulose, sodium starch glycolate, and cross-linked polymers, preferably, crospovidone. The amounts of each excipient used are conventional and can be determined by routine experimentation.

Compression into a tablet form can be accomplished by a tablet press. A tablet press includes a lower punch that fits into a die from the bottom and an upper punch having a corresponding shape and dimension which enters the die cavity from the top after the tabletting material falls into the die cavity. The tablet is formed by pressure applied on the lower and upper punches. Typical compression pressures are about 6 kN to about 36 kN and will vary based on the desired size and hardness of the tablet. Preferably the compression pressure is about 8 kN to about 20 kN. Tablet presses and other compression devices are well known in the art.

For ease of swallowing, it may be desirable to coat the tablet containing gabapentin. Examples of acceptable commercial coating processes are described in "The Theory and Practice of Industrial Pharmacy, $3^{rd}$ ed.", Lachman Lieberman, Kanig, pp. 359–373, which is incorporated by reference. Coating materials may include polymers such as hydroxypropyl methylcellulose, ethylcellulose, povidone, and polyethylene glycol; plasticizers such as castor oil, glycol and propylene glycol; and colorants such as dyes and lakes of dyes. Commercially available color coating systems such as Opadry® systems (Colorcon) may be also be used.

Capping and lamination are defects that appear during compression. A capping defect means that there is partial or complete separation of the top or bottom crowns of a tablet from the main body. A lamination defect means that there is separation of a tablet in two or more layers.

Friability and hardness are characteristics used to determine the mechanical strength of the tablets. Friability refers to the tablet resistance to surface abrasion. Hardness or crushing strength refers to the force required to fracture the tablet.

The tablet must be of sufficient crushing strength or hardness to withstand the coating process without chipping or breaking. The hardness of the tablets prepared in accordance with the present invention can be measured by known methods as described, for example, in, "The Theory and Practice of Industrial Pharmacy, $3^{rd}$ ed.", Lachman Lieberman, Kanig, incorporated herein by reference. Hardness or crushing strength is the amount of force required to fracture the tablet. Typically a larger tablet requires a higher hardness to withstand the mechanical shocks of processing as well as subsequent consumer handling. However, the hardness should not be so high that it adversely effects disintegration and dissolution rates of the tablets. Preferably, the hardness of the gabapentin tablets is about 10 kp to about 20 kp. More preferably, the hardness of the gabapentin tablets is about 14 kp to about 15 kp.

Another measure of durability of the tablet is the test for friability. Friability is the resistance to surface abrasions and is exemplified by tests which measure weight loss of the tablet by subjecting the tablets to standardized agitation procedures such as provided by the Roche Friabilator where the initial weight of tablets (W(i)) subjected to 100 free falls of 6 inches in a rotating drum are then weighed (W). The friability, f, is given by the formula, $f=100\times(1-W/W(i))$. A friability values of about 1% is acceptable, but friability below about 0.8% is preferred.

The poor compactibility and compressibility properties of gabapentin are illustrated in FIG. 1 which is a plot of tablet hardness versus compression force for tablets made by: dry granulation (▲), wet granulation (●), and the present invention (♦). The composition of the tablets is identical and differs only in the method of manufacture. The composition of the tablets comprise: 88.9% gabapentin, 3.5% hydroxypropyl cellulose, 5.8% crospovidone and, 1.8% calcium stearate (expressed as w/w of the tablet weight).

In the dry granulation process, gabapentin, hydroxypropyl cellulose, crospovidone, and calcium stearate were sieved through a 20 mesh sieve and blended together in a V-blender. The resulting blend was then slugged on a tablet press using ½ inch round flat-faced punches. The slugs were ground through an 18 mesh sieve using an oscillator and then compressed into tablets. This process produced tablets that had low hardness and a friability of 100% because every tablet exhibited breakage such as capping. As FIG. 1 demonstrates, the tablets produced by this method had a maximum hardness less than 3 kp.

In the wet granulation process, gabapentin was placed in a high shear mixer-granulator and mixed with a solution containing 10% hydroxypropyl cellulose in alcohol. The wet material was dried in a fluid-bed dryer and then milled through a comminuting mill equipped with a perforated plate with 0.0020" diameter holes. The milled material was placed back in the granulator and another portion of the hydroxypropyl cellulose solution was added while mixing. This wet material was again dried and mixed. This cycle was repeated until all of the binder solution was incorporated into the granulation. The milled granules were then blended with crospovidone and calcium stearate in a V-blender and compressed into tablets on a high speed, force fed tablet press. Tablets produced by the wet granulation process achieved a maximum hardness of only 11 kp and exhibited an unacceptable friability level of 2.0%. Furthermore, because of the multiple applications of binder solution and intermittent drying, the gabapentin particles were subjected to a large amount of moisture and heat which is detrimental to the stability of gabapentin.

Attempts to improve both the wet and dry granulation methods involved the addition of compression aids such as microcrystalline cellulose, calcium phosphate salts or mannitol and increasing the ratio of binder to drug to 1:6. Although these attempts resulted in improved hardness, the tablets were too large and had a friability value approaching 100% due to abrasions and capping.

Figure 2:
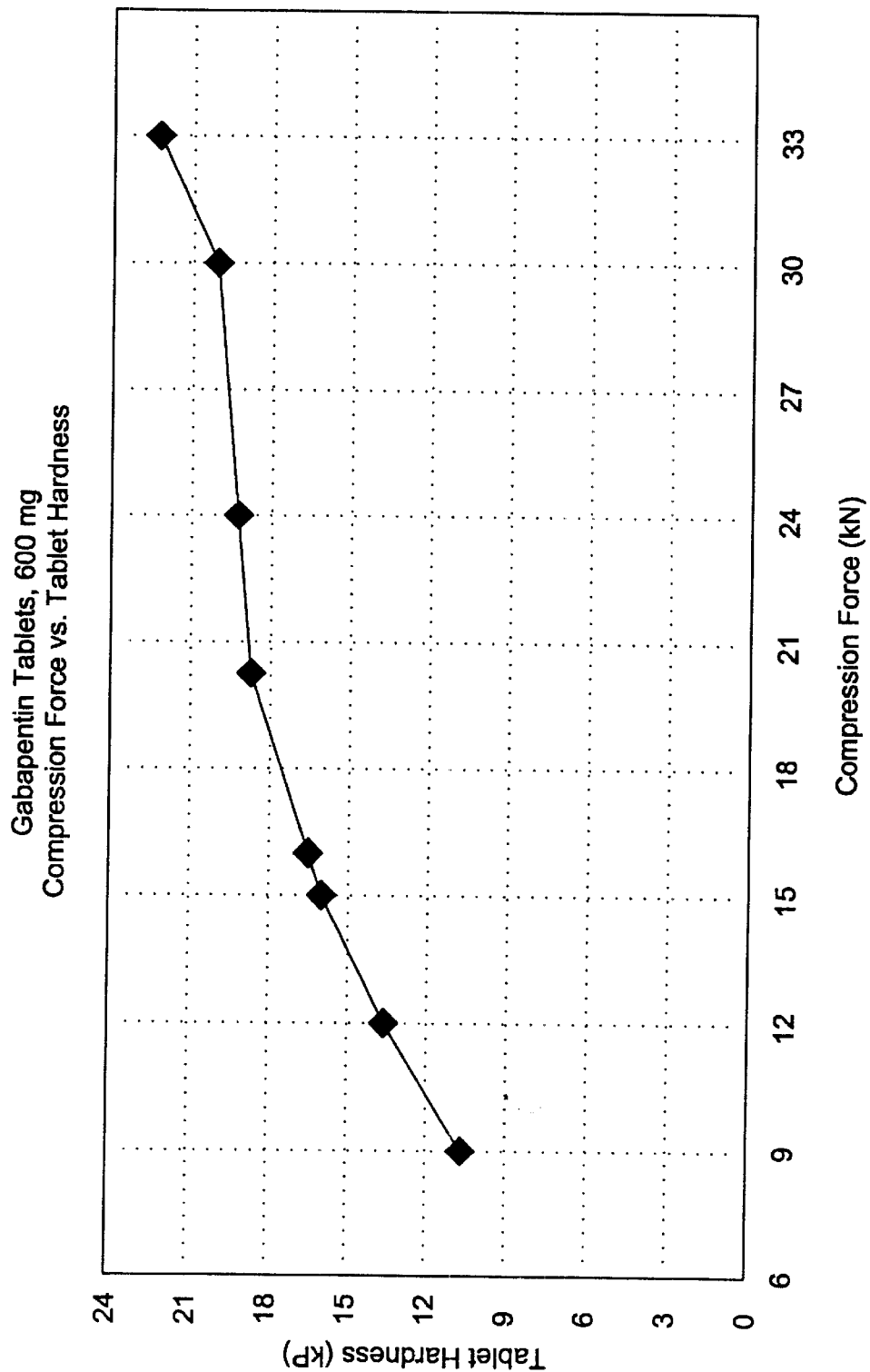
FIGS. 2 and 3 show a plot of tablet hardness versus compression force for tablets containing, respectively, 600 mg and 800 mg of gabapentin made in accordance with Example 1.
Figure 3:
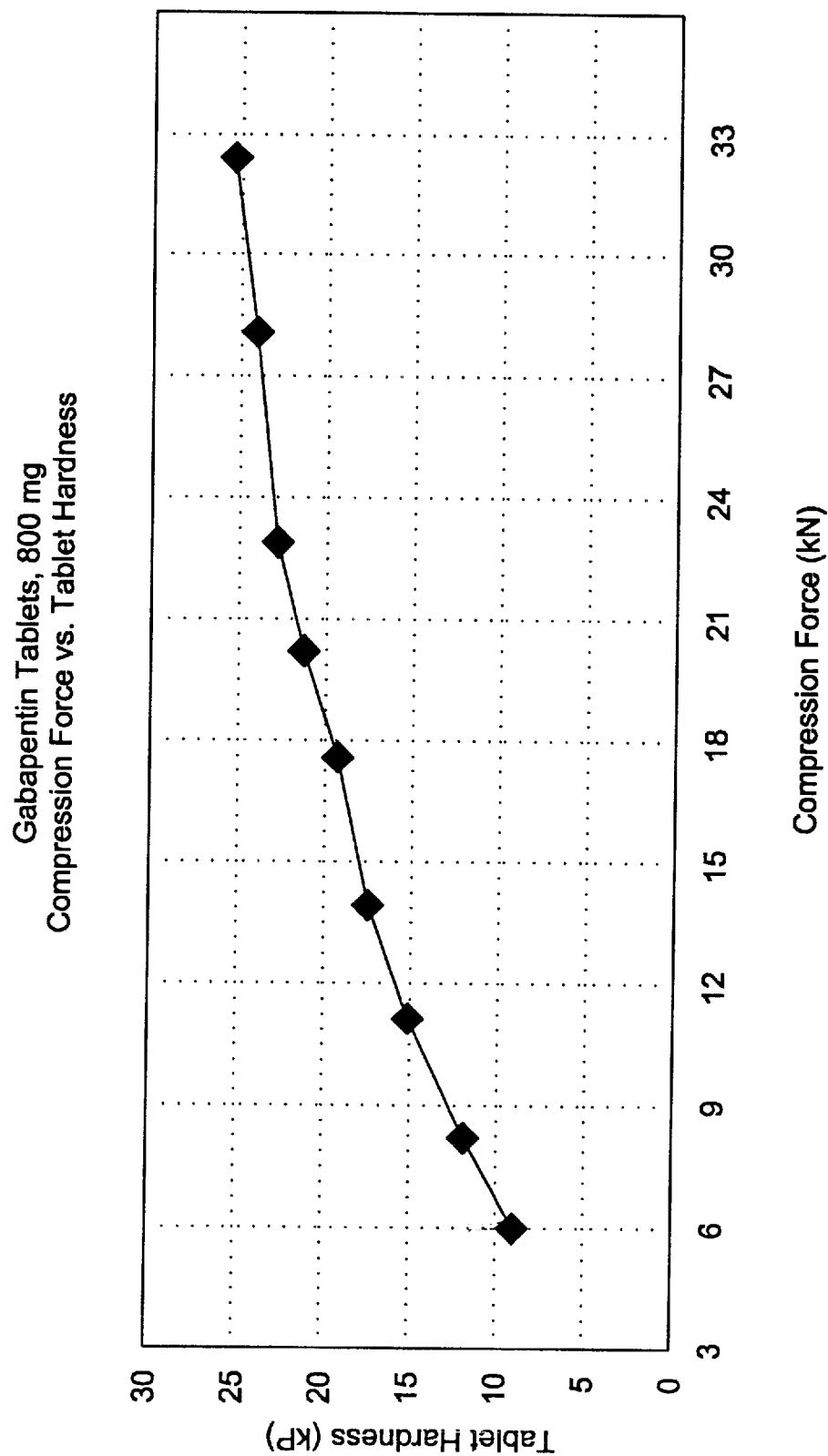

The 600 mg tablets produced by the present invention achieved a desired hardness strength of 14 kp and a friability of 0.01%. As shown in FIG. 2, the 600 mg tablets made in accordance with Example 1 had a range of 10 kp to 22 kp. The 800 mg tablets produced by the present invention achieved a desired hardness strength of 16 kp and a friability of 0.04%. The hardness range of the 800 mg tablets made in accordance with Example 1 was 10 kp to 25 kp as show in FIG. 3. Furthermore, this one set spray-coat application of binder solution did not require excess excipients, moisture, or heat which can be detrimental to the stability of gabapentin.

The following Examples of this invention are for illustrative purposes and are not intended to limit the scope of the invention.

TABLE 1

Composition of a 600 mg Gabapentin Tablet

| INGREDIENT | AMOUNT PER TABLET |
|---|---|
| Gabapentin | 600 mg |
| Hydroxypropyl Cellulose, NF 75–150 cps (Klucel LF) | 24 mg |

TABLE 1-continued

Composition of a 600 mg Gabapentin Tablet

| INGREDIENT | AMOUNT PER TABLET |
|---|---|
| Crospovidone (Polyplasdone XL) | 39 mg |
| Calcium Stearate | 12 mg |
| TOTAL WEIGHT | 675 mg |

TABLE 2

Composition of a 800 mg Gabapentin Tablet

| INGREDIENT | AMOUNT PER TABLET |
|---|---|
| Gabapentin | 800 mg |
| Hydroxypropyl Cellulose, NF 75–150 cps (Klucel LF) | 32 mg |
| Crospovidone (Polyplasdone XL) | 52 mg |
| Calcium Stearate | 16 mg |
| TOTAL WEIGHT | 900 mg |

TABLE 3

Composition of a 800 mg Gabapentin Tablet

| INGREDIENT | AMOUNT PER TABLET |
|---|---|
| Gabapentin | 800 mg |
| Copolyvidone | 32 mg |
| Crospovidone (Polyplasdone XL) | 52 mg |
| Calcium Stearate | 16 mg |
| TOTAL WEIGHT | 900 mg |

EXAMPLE 1

Gabapentin tablets of the present invention are produced by applying a coating of binder solution comprising hydroxypropyl cellulose dissolved in alcohol, through a pneumatically atomized nozzle. The binder solution containing 7.5% hydroxypropyl cellulose is prepared by slowly adding hydroxypropyl cellulose, to alcohol and mixing the solution at room temperature for approximately 60 minutes or until the binder is uniformly dispersed and a clear homogenous solution is achieved.

Gabapentin, supplied by Teva Tech, Ltd (Israel) and having a particle size in the range of 10 μm to 125 μm, is loaded into the product container of a fluid-bed processor. The fluid bed parameters are set as follows:

| | |
|---|---|
| Number of Nozzles: | 1 |
| Inlet Air Temperature Set Point: | 50° C. |
| Atomization Air Pressure: | 2–4 Bar |
| Process Air Volume Set Point Range: | 100 cfm–400 cfm |
| Spray Rate Range: | 100 g/min–300 g/min |
| Product Temperature: | 12° C.–25° C. |

The process air volume is set to 100 cfm and gabapentin is fluidized. When the product temperature reaches about 25° C. to about 28° C., the binder solution is applied. This solution is introduced through a pneumatically atomized nozzle positioned in the expansion chamber of the fluid bed processor. The fluidized gabapentin particles are thus coated with the binder solution.

While spraying, the process air volume is increased until the product temperature is stabilized between 12° C.–25° C. Once all the binder solution is applied, the process air volume is set to 150 cfm and the temperature to about 35° C. to dry the coated particles. Drying is complete when the loss on drying, determined by Computerized Moisture Analyzer Balance, is not more than 0.75%.

The spray-coated particles are then sized through a Comminuting Mill. These sized particles are mixed in a V-Blender with crospovidone and calcium stearate to produce a final blend. The final blend is then compressed into tablets on a force fed tablet press at a pressure of 12 kN to 14 kN. The hardness range of the 600 mg tablets was 13.3 kp to 14.9 kp with an average hardness of 14.2 kp. Optionally, the tablets can be aesthetically coated with an aqueous dispersion such as an Opadry® (Colorcon) color system.

As used in the claims, gabapentin shall mean gabapentin itself, gabapentin analogs, all pharmaceutically acceptable salts of gabapentin, all pharmaceutically acceptable salts of gabapentin analogs, all combinations of pharmaceutically acceptable salts of gabapentin, all combinations of pharmaceutically acceptable gabapentin analogs, or all combinations of gabapentin itself with its pharmaceutically acceptable salts.

What is claimed is:

1. An immediate release, pharmaceutical tablet comprising more than about 76% by weight of gabapentin and a binder.

2. A pharmaceutical tablet of claim 1 comprising more than about 88% by weight of gabapentin.

3. A pharmaceutical tablet of claim 1 wherein the tablet has a friability of less than about 0.8%.

4. A pharmaceutical tablet of claim 1 wherein the tablet has a hardness of about 14 kp to about 16 kp.

5. A pharmaceutical tablet of claim 1 wherein the tablet has a lactam level of less than about 0.2%.

6. A pharmaceutical tablet comprising:

(a) more than about 76% by weight of gabapentin and a binder;

(b) a friability of less than about 1%.

(c) a hardness of about 10 kp to about 20 kp; and (d) a lactam level of less than about 0.4% by weight of the tablet.

7. A pharmaceutical tablet comprising more than about 76% by weight of gabapentin and a binder, wherein the tablet has friability of less than about 0.8%.

8. A pharmaceutical tablet comprising more than about 76% by weight of gabapentin and a binder, wherein the tablet has a hardness of about 14 kp to about 16 kp.

9. A pharmaceutical tablet comprising more than about 76% by weight of gabapentin and a binder, wherein the tablet has a lactam level of less than about 0.2%.

10. An immediate release, pharmaceutical tablet comprising:

(a) more than about 76% by weight of gabapentin and a binder;

(b) a friability of less than about 1%, (c) a hardness of about 10 kp to about 20 kp; and (d) a lactam level of less than about 0.4% by weight of the tablet.

* * * * *